United States Patent [19]

Gane

[11] 4,225,517

[45] Sep. 30, 1980

[54] PROCESS FOR THE PRODUCTION OF ACETALDEHYDE BY THE REACTION OF METHANOL WITH SYNTHESIS GAS

[75] Inventor: Brian R. Gane, Weybridge, England

[73] Assignee: The British Petroleum Company Limited, London, England

[21] Appl. No.: 957,701

[22] Filed: Nov. 6, 1978

[30] Foreign Application Priority Data

Nov. 8, 1977 [GB] United Kingdom ............... 46329/77
May 13, 1978 [GB] United Kingdom ............... 19414/78

[51] Int. Cl.$^3$ ...................... C07C 45/49; C07C 47/06
[52] U.S. Cl. ................................................ 568/487
[58] Field of Search ........ 260/603 R, 601 R, 604 HF, 260/604 AC; 568/902

[56] References Cited

U.S. PATENT DOCUMENTS 3,356,734  12/1967  Kuraishi et al. ................. 260/601 R

OTHER PUBLICATIONS

Abstract of Mitsubishi Gas Chem. Ind. JA 049557.

*Primary Examiner*—Werren B. Lone

*Attorney, Agent, or Firm*—Brooks, Haidt, Haffner & Delahunty

[57] ABSTRACT

Acetaldehyde is produced by reacting methanol with hydrogen and carbon monoxide at elevated temperature and pressure in the presence of a catalyst cobalt, an iodide or a bromide and one of the elements arsenic, antimony or bismuth, in the form of a compound thereof, and in the additional presence of one or more of the following additives:

(i) an inert liquid such as chlorobenzene, decanoic acid, a polydimethylsiloxane fluid or a methyl phenyl silicone fluid, (ii) an acid and/or an acid derivative such as acetic acid, acetic anhydride, propionic acid, phenylacetic acid, benzoic acid, methyl acetate or butyl acetate.

(iii) and oxygen-containing organic compound such as 1,4-dioxane, tetrahydrofuran, di-n-propylether, diphenylether, acetone, acetaldehyde, n-propanol or n-butanol.

(iv) a non-polar solvent such as an alkane, benzene or an alkyl-substituted benzene.

The presence of the additive suppresses by-product formation and thereby improves the yield and selectivity to acetaldehyde.

14 Claims, No Drawings

PROCESS FOR THE PRODUCTION OF ACETALDEHYDE BY THE REACTION OF METHANOL WITH SYNTHESIS GAS

The present invention relates to a process for the production of acetaldehyde from methanol and synthesis gas (mixtures of carbon monoxide and hydrogen) in the presence of a cobalt-containing catalyst.

Acetaldehyde is a valuable industrial product which is principally produced by the direct oxidation of ethylene or light hydrocarbons, and as a by-product of the vinyl acetate process. Acetaldehyde is also produced by the vapour phase oxidation or dehydrogenation of ethanol. The importance of acetaldehyde lies in its use as an intermediate in the manufacture of other organic chemicals, for example, acetic acid, acetic anhydride, pentaerythritol, butanol, chloral, 2-ethylhexanol, and metaldehyde.

The rapidly dwindling reserves of crude oil from which ethylene is derived and the associated need to utilise fully the remaining natural resources such as coal and the vast amounts of gases, eg methane, potentially available from the exploitation of North Sea oilfields has stimulated researchers to investigate other routes to acetaldehyde utilising these materials as feedstocks. Both coal and methane gas can be converted into synthesis gas (CO+H$_2$), which in turn can be reacted to form methanol, which methanol can be further reacted with carbon monoxide and hydrogen under appropriate conditions to form acetaldehyde. The course of this reaction can be represented by the following equation:

$$CH_3OH + CO + H_2 \rightarrow CH_3CHO + H_2O$$

The provisional specification accompanying our application No. 957,700 filed Nov. 6, 1978 describes a process for the production of ethanol by reacting methanol with hydrogen and carbon monoxide in the presence of an inert liquid and a catalyst comprising cobalt, an iodide or a bromide and a compound having the formula:

wherein X is nitrogen, phosphorus, arsenic or antimony and A, B and C are individually monovalent organic radicals or X is phosphorus, arsenic or antimony and any two of A, B and C together form an organic divalent cyclic ring system bonded to the X atom or X is nitrogen and all of A, B and C together form an organic trivalent cyclic ring system bonded to the X atom. The term inert liquid, as used in that specification, means a compound which does not poison or otherwise adversely affect the catalyst and which is mainly in the liquid form under the conditions of the reaction. Furthermore, the inert liquid is capable of forming a separate phase in the presence of methanol containing up to 20% w/w water under normal conditions of temperature and pressure and is further characterised by having in its molecular structure bonds such as carbon/oxygen, carbon/sulphur, carbon/halogen, carbon/nitrogen, or carbon/silicon as well as normal carbon/carbon and carbon/hydrogen bonds ie the inert liquid contains one or more atoms other than carbon and hydrogen. An example of such an inert liquid is chlorobenzene.

Whilst the major realisable product of the process described, using a phosphorus compound as a component of the catalyst, is ethanol, a finite amount of acetaldehyde is also formed. Further investigation of the process described has shown that using arsenic or antimony containing catalysts the product distribution is shifted in the direction of acetaldehyde formation and, moreover, the reaction is not restricted to the addition of an inert liquid, nor to arsenic or antimony-containing catalysts. We have found that the incorporation in the process of a variety of additives which fall under the broad description of inert solvents, monocarboxylic acids and/or derivatives thereof, co-ordinating solvents and non-polar solvents can increase the total realisable yield and selectivity, as hereinafter defined, to acetaldehyde.

Thus according to the present invention there is provided a process for the production of acetaldehyde which process comprises reacting, at elevated temperature and pressure, methanol with hydrogen and carbon monoxide in the presence of:

(a) a catalyst comprising cobalt, an iodide or a bromide and one of the elements arsenic, antimony and bismuth, in the form of a compound thereof, and (b) an additive which comprises either:
  (i) an inert liquid as hereinafter defined and/or
  (ii) an acid and/or a derivative thereof having the formula:

wherein the substituent R is a hydrocarbyl group or an oxygen-containing hydrocarbyl group and the substituent X is the group —OR$^1$ wherein R$^1$ is a hydrogen atom, a hydrocarbyl group or an oxygen-containing hydrocarbyl group or X is the group —O—CO—R$^2$ wherein R$^2$ is a hydrocarbyl group or an oxygen-containing hydrocarbyl group, and/or (iii) one or more oxygen-containing organic compound(s) comprising compounds containing at least one of the groups:

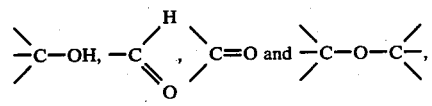

and/or (iv) a non-polar solvent.

By total realisable yield of acetaldehyde within the context of the specification is meant the yield of free acetaldehyde plus the yield of acetaldehyde realisable by the hydrolysis of acetaldehyde-yielding compounds (eg dimethyl acetal). In the same way, by realisable methanol is meant the free methanol plus the methanol realisable by the hydrolysis of methanol-yielding esters (eg, methyl acetate) plus the methanol realisable by the hydrolysis of dimethyl acetal. Thus, % Molar Yield of Realisable Acetaldehyde =

-continued
$$\text{\% Molar Selectivity to Realisable Acetaldehyde} = \frac{\text{Moles of realisable methanol converted into realisable acetaldehyde} \times 100}{\text{Total moles of realisable methanol fed}}$$

and, $$\text{\% Molar Selectivity to Realisable Acetaldehyde} = \frac{\text{Moles of realisable methanol converted into realisable acetaldehyde} \times 100}{\text{Total moles of realisable methanol converted}}$$

By the yield of realisable acetic acid is meant the yield of free acetic acid plus the yield of acetic acid realisable by the hydrolysis of acetic acid-yielding esters (eg, methyl acetate). In calculating the yield it is assumed that all the acetic acid is derived from methanol and synthesis gas and no account is taken of acetic acid derived from cobalt acetate when this is added as catalyst.

Thus, $$\text{\% Molar Yield of Realisable Acetic Acid} = \frac{\text{Moles of realisable methanol converted into realisable acetic acid} \times 100}{\text{Total moles of realisable methanol fed}}$$

By the yield of realisable ethanol is meant the yield of free ethanol plus the yield of ethanol realisable by the hydrolysis of ethanol-yielding esters.

$$\text{\% Molar Yield of Realisable Ethanol} = \frac{\text{Moles of realisable methanol converted into realisable ethanol}}{\text{Total moles of realisable methanol fed}} \times 100$$

$$\text{\% Methanol Conversion} = \frac{\text{Total moles of methanol converted}}{\text{Total moles of methanol fed}} \times 100$$

Methanol is a readily available industrial product. It is generally manufactured on an industrial scale from synthesis gas. Whilst it is preferred that the methanol be substantially pure the presence of small amounts of certain impurities can be tolerated. The methanol may contain up to 50% by weight of water.

Mixtures of the gases hydrogen and carbon monoxide are abundantly available in the form of synthesis gas. Methods for preparing synthesis gas are well-known in the art and usually involve the partial oxidation of a carbonaceous substance, eg coal. Alternatively synthesis gas may be prepared, for example, by thermal steam reforming of methane. For the purpose of the present invention the molar ratio of carbon monoxide to hydrogen may suitably be in the range 2:1 to 1:3, preferably 3:2 to 2:3. Methods for adjusting the molar ratio of carbon monoxide to hydrogen are well-known to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

The catalyst (a) comprises cobalt, an iodide or bromide and one or more of the elements arsenic, antimony and bismuth, in the form of a compound thereof. Any source of cobalt which will react with carbon monoxide/hydrogen mixtures to yield a cobalt carbonyl or carbonyl hydride complex can be used in the process of the present invention. Cobalt is preferably employed in the ionic form, but the use of cobalt metal to react in situ to form ionic cobalt which then further reacts to form the desired cobalt complex is within the scope of the present invention. Typical sources of cobalt are, for example, compounds such as cobalt acetate, cobalt formate, cobalt propionate and the like, which under the reaction conditions form carbonyl or carbonyl hydride complexes. The compounds may be in the hydrated or anhydrous forms. The iodide or bromide can be added either in ionic form eg as cobalt iodide or cobalt bromide or as molecular iodine ($I_2$) or bromine ($Br_2$), or as an alkyl or aryl iodide or bromide, preferably methyl iodide. However, the iodide or bromide may also be added in ionic form utilising cations which are inert with regard to the hydrocarbonylation reaction. Typical of the inert form is potassium iodide or bromide, sodium iodide or bromide and lithium iodide or bromide.

The arsenic, antimony or bismuth is added in the form of a compound thereof. The compound may be, for example, an iodide. Preferably the compound has the formula:

(II)

wherein X is arsenic, antimony or bismuth and A, B and C are individually monovalent organic radicals or any two of A, B and C together form an organic divalent cyclic ring system bonded to the X atom. Preferably the compound having the formula (II) is:

(III)

wherein X is arsenic, antimony or bismuth and $R^3$ independently is an organo group containing from 1 to 20 carbon atoms, is preferably free from aliphatic carbon-carbon unsaturation, and is bonded to the X atom by a carbon/X bond. The organo group $R^3$ in the compound of formula (III) is preferably a hydrocarbyl group which may be a saturated aliphatic, a saturated cycloaliphatic, an aromatic, a substituted saturated aliphatic, a substituted saturated cycloaliphatic or a substituted aromatic group of which the unsubstituted saturated and aromatic groups are preferred. The substituents are preferably free from aliphatic carbon-carbon unsaturation and may contain, besides atoms of carbon and hydrogen, other atoms such as oxygen, sulphur and halogen, in particular halogen of atomic number from 9 to 35, provided that such atoms are not directly bonded to phosphorus. Illustrative of suitable saturated aliphatic $R^3$ groups are hydrocarbyl $R^3$ groups such as methyl, ethyl, propyl, isopropyl, butyl, isoctyl, decyl, dodecyl, octadecyl, cyclohexyl, cyclopentyl, 3,4-dimethyl cyclopentyl, cyclooctyl, benzyl and β-phenylethyl. Aromatic $R^3$ groups include hydrocarbyl aromatic groups such as phenyl, tolyl, xylyl, p-ethylphenyl, p-tert-butylphenyl, m-octyl phenyl, 2,4-diethylphenyl, p-phenylphenyl, m-benzylphenyl and 2,4,6-trimethylphenyl. Preferably the $R^3$ group is the phenyl group.

In the compound of formula (III) the $R^3$ moieties may be the same or different, although for economic reasons they are preferably identical. Exemplary compounds having the formula (III) are triphenylarsine, triphenylstibine, triphenyl bismuth, tributylarsine and tributylstibine.

The term "hydrocarbyl" has been used throughout the foregoing in its accepted meaning as representing a radical formed from a hydrocarbon by removal of a hydrogen atom.

The exact nature of the catalysts of this invention under the reaction conditions is not known but they are thought to be arsine, stibine or bismuth-containing ligand/cobalt carbonyl/hydride/halide complexes. The cobalt is thought to be in a reduced state but its exact valency is not known. The catalyst may be prepared by first reacting the individual components together and then adding the mixture to the reaction vessel, or by adding the individual components to the reaction vessel and allowing the catalyst to form under the reaction conditions. During formation of the catalyst it may be advantageous to use pressures higher than those employed in the subsequent hydrocarbonylation reaction, particularly when reaction pressures of about 100 bar are employed.

The molar ratio of cobalt to iodine or bromine in the catalyst may be in the range from 1:3 to 10:1, preferably from 1:1 to 5:1. The molar ratio of cobalt to the compound of formula (II) may be in the range of from 2:1 to 1:20, preferably from 1:1 to 1:10. The molar ratio of iodine or bromine to the compound of formula (II) may be in the range from 2:1 to 1:10, preferably from 1:1 to 1:8. The molar ratio of cobalt to methanol may be in the range of from 1:10 to 1:1000, preferably from 1:40 to 1:800.

The additive (b) may be an inert liquid. The term, inert liquid, as used in this specification means a compound which does not poison or otherwise adversely affect the catalyst, is mainly in liquid form under the conditions of the reaction, is capable of forming a separate phase in the presence of methanol containing up to 20% w/w water under normal conditions of temperature and pressure and is further characterised by having in its molecular structure one or more atoms other than carbon and hydrogen. Thus the inert liquid typically contains bonds such as carbon/oxygen, carbon/sulphur, carbon/halogen, carbon/nitrogen, or carbon/silicon as well as normal carbon/carbon and carbon/hydrogen bonds. Thus the compound may be, for example, an aryl halide, an ether, a thiophene, a long chain acid, an aromatic acid or a silicone oil. An example of a suitable long chain acid is decanoic acid. Typical of the silicone oils which may be used are polydimethylsiloxane fluids and methyl phenyl silicone fluids. Specific silicone fluids which have been found useful in the process are the DC 200 series of fluids supplied by Dow Corning. Those compounds that are capable of forming, under normal conditions of temperature and pressure, a separate phase in the presence of methanol containing up to 20% w/w water but otherwise poison or adversely affect the catalyst (ie, non-inert compounds) are not included within the scope of the present invention. The molar ratio of methanol to inert liquid may be varied within wide limits, eg in the range from 30:1 to 1:10, preferably from 25:1 to 1:2. In the case of silicone oils for which the molecular weight is not known with any degree of certainty the volume of oil added/volume of methanol may be in the range 0.05:50, preferably from 0.1 to 5 v/v.

According to another aspect of the present invention there is provided a process for the production of acetaldehyde which process comprises reacting at elevated temperature and pressure methanol with hydrogen and carbon monoxide in the presence of an additive in the form of an inert liquid as hereinbefore defined and a catalyst comprising cobalt, an iodide or a bromide and a compound having the formula:

wherein $X^1$ is arsenic or antimony and $A^1$, $B^1$ and $C^1$ are individually monovalent organic radicals or any two of $A^1$, $B^1$ and $C^1$ together form an organic divalent cyclic ring system bonded to the $X^1$ atom. Examples of compounds having the formula (IV) are triphenylarsine, triphenylstibine and tri-n-butylarsine.

In the acid or acid derivative of formula (I) the substituents R, $R^1$ and $R^2$ may independently be hydrocarbyl groups or oxygen-containing hydrocarbyl groups. The hydrocarbyl group is preferably free from carbon-carbon unsaturation. Thus the hydrocarbyl group may suitably be a saturated aliphatic group, a saturated cycloaliphatic group or an aromatic group. Preferably the hydrocarbyl group is an alkyl group containing from 1 to 20, preferably from 1 to 6 carbon atoms. Tthe substituent X in the formula (I) may be either an alkoxy group —$OR^1$, in which case the additive is an ester, or a hydroxyl group —OH, in which case the additive is a monocarboxylic acid, or a carboxyl group —O—CO—$R^2$, in which case the additive is an acid anhydride. Preferably the substituent X is the group —$OR^1$ in which $R^1$ is either a hydrogen atom or an alkyl group containing from 1 to 20, preferably from 1 to 6 carbon atoms. Suitable compounds having the structural formula (I) are acetic acid, acetic anhydride, propionic acid, decanoic acid, phenylacetic acid, benzoic acid, methyl acetate and butyl acetate. Preferred compounds having the structural formula (I) are acetic acid and methyl acetate. It will of course, be appreciated that when the compound having the structural formula (I) is added as the free acid or anhydride it will largely be present in the reaction mixture as an ester as a result of reaction with methanol or other alcohol. The acid or acid derivative of structural formula (I) may be added in an amount such that the molar ratio of additive to free methanol can be as high as 1.5:1, but is normally in the range from 0.1:1 to 0.7:1.

Preferably the oxygen-containing organic compound is one which exists mainly in the form of a liquid under the reaction conditions employed. Furthermore the compound is preferably one which is miscible with methanol containing up to 20% w/w water under normal conditions of temperature and pressure. Certain of the compounds falling within the scope of the present invention may be reduced or hydrolysed under the reaction conditions employed. For example, certain ethers may be hydrolysed to alcohols. Whilst such compounds may be used in the process of the invention it is preferred to add compounds which are not so affected. Whilst the oxygen-containing organic compound containing a

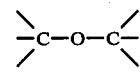

group may be an aliphatic, alicyclic or aromatic ether it is preferred that those compounds containing

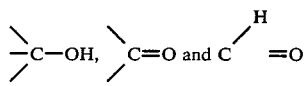

groups are, respectively, aliphatic alcohols, aliphatic ketones and aliphatic aldehydes. Oxygen-containing organic compounds which may be added include, for example, 1,4-dioxane, tetrahydrofuran, di-n-propylether, diphenylether, acetone, acetaldehyde, n-propanol and n-butanol. The oxygen-containing organic compound may be added in an amount such that the molar ratio of methanol to the oxygen-containing organic compound contacted with the catalyst is in the range from 20:1 to 1:3, preferably from 10:1 to 1:1.

Whilst it is appreciated that both acids and acid derivatives having the formula (I) and oxygen-containing organic compounds may be formed as by-products during the course of the reaction one aspect of the invention resides in the addition of one or other or both to the reaction. By so-doing the amount of undesirable side reaction is reduced, with the attendant consequence that the yield and selectivity to acetaldehyde is increased.

Alternatively, or in addition, the additive may be a non-polar solvent. Suitable non-polar solvents include alkanes, benzene and alkyl-substituted benzenes as disclosed in U.S. patent application Ser. No. 585276. The molar ratio of methanol to non-polar solvent may suitably be in the range of from 30:1 to 1:10, preferably from 25:1 to 1:2.

Methanol may suitably be reacted with carbon monoxide and hydrogen at any temperature in the range from 150 to 250, preferably from 165 to 210, even more preferably from 165° to 190° C., and at a pressure greater than 80 bar, preferably in the range from 100 to 300 bar.

The process may be carried out batchwise or continuously, continuous operation being preferred. The process may be carried out continuously for example by feeding methanol and synthesis gas to a reactor containing the catalyst and the additive, removing from the reactor a liquid product containing acetaldehyde, by-products including ethanol and dimethyl acetal, unchanged methanol, catalyst and unreacted synthesis gas, separating the synthesis gas which may be recycled to the reactor, removing light ends including ethers, separating the product containing acetaldehyde and by-products from the catalyst and thereafter recovering acetaldehyde from the by-products, there being recycled to the reactor the catalyst, methanol and additive. Other reaction by-products, particularly those which can act as precursors for the formation of acetaldehyde, may also be recycled to the reactor with advantage. It may be necessary to feed from time to time further catalyst.

The residence time may suitably be up to 8 hours, but is preferably in the range of from 10 to 180 minutes. Short residence times are preferred because long residence times may lead to further reaction of the acetaldehyde product by aldol condensation-type reaction giving, for example, n-butyraldehyde. Within the context of the specification the residence time for batchwise operation is that time during which the reactor is at the specified reaction temperature. When the process is operated continuously the residence time is calculated as follows:

$$\text{Residence Time (Hours)} = \frac{\text{Volume of the reactor occupied by the liquid phase at } STP \text{ (liters)}}{\text{Total flow of liquid into the reactor (liters/hour at } STP\text{)}}$$

With regard to the various ratios of reactants to be employed in the process of the invention it has already been stated that the methanol may contain up to 50% by weight of water. In certain circumstances the addition of water may be beneficial to the reaction ie, the ratio of methanol to water in the feed can be adjusted so that two phases are present either at the start or at the end of the reaction or both. In both continuous and batch operations the molar ratio of methanol to carbon monoxide plus hydrogen (synthesis gas) fed may be in the range of from 10:1 to 1:20 preferably from 2:1 to 1:5.

The invention will now be illustrated by reference to the following Examples.

EXAMPLE 1

A stainless steel, magnetically-stirred autoclave equipped for pressurised reactions was charged under nitrogen with methanol (0.80 mole) containing cobalt acetate tetrahydrate (0.01 mole), iodine (0.005 mole) and triphenylarsine (0.0175 mole). To this mixture was further added 0.633 mole chlorobenzene (which is an inert liquid).

The system was purged with nitrogen, then pressurised to 200 bar with a mixture of carbon monoxide and hydrogen (1:1 molar). The reactor temperature was then raised to 205° C. and maintained at this temperature for 2 hours. When heating was started the pressure in the reactor rose above 200 bar and then began to decrease as the reaction commenced. During the course of the reaction, whenever the pressure in the autoclave fell to 140 bars a fresh charge of carbon monoxide and hydrogen (1:1 molar mixture) was added thereby increasing the reactor pressure to 200 bars. After two hours at 205° C. the autoclave was allowed to cool and the reaction product was analysed. The reactants and their concentrations are given in Table 1A and the results are given in Table 1B.

Comparison Test 1

The procedure described in Example 1 was followed, except that no chlorobenzene was added. The reactants and their concentrations are given in Table 1A and the results obtained are shown in Table 1B.

This is not an example according to the present invention because no additive was employed. The example is included for the purpose of comparison only.

Comparison Test 2

The procedure described in Example 1 was followed except that triphenylarsine was replaced by triphenylphosphine. The reactants and their concentrations are given in Table 1A and the results obtained are shown in Table 1B.

This is not an example according to the invention because a phosphorus compound formed a component of the catalyst. The example is included for the purpose of comparison only.

Comparison Test 3

The procedure described in Example 1 was followed except that a smaller quantity of chlorobenzene was used and triphenylarsine was replaced by triphenylphosphine. The reactants and their concentrations are given in Table 2A and the results obtained are shown in Table 2B.

This is not an example according to the invention because a phosphorus compound formed a component of the catalyst. The example is included for the purpose of comparison only.

EXAMPLE 2

The procedure described in Example 1 was followed except that a smaller quantity of chlorobenzene was used and triphenylarsine was replaced by triphenylstibine. The reactants and their concentrations are shown in Table 2A and the results are shown in Table 2B.

Comparison Test 4

The procedure described in Example 1 was followed except that the reactor temperature was raised only to 185° C. and maintained at that temperature for 1 hour only. Furthermore the triphenylarsine was replaced by triphenylstibine and no chlorobenzene was added. The reactant concentrations are shown in Table 2A and results obtained are shown in Table 2B.

This is not an example according to the present invention because no additive was present in the initial reaction mixture. It is included for the purpose of comparison only.

EXAMPLE 3

The procedure described in Comparison Test 4 was followed except that a small amount of chlorobenzene was added. The reactant concentrations are shown in Table 2A and the results obtained are shown in Table 2B.

EXAMPLE 4

The procedure described in Example 3 was followed except that instead of chlorobenzene there was added methyl acetate. The reactant concentrations are shown in Table 2A and the results obtained are shown in Table 2B.

EXAMPLE 5

The procedure described in Example 3 was followed except that instead of chlorobenzene there was added octane. Furthermore the triphenylstibine component of the catalyst was replaced by triphenylarsine. The reactant concentrations are shown in Table 3A and the results obtained are shown in Table 3B.

EXAMPLE 6

The procedure described in Example 3 was followed except that instead of chlorobenzene there was added acetone. Furthermore the triphenylstibine component of the catalyst was replaced by triphenylarsine. A faulty valve necessitated an estimation of the hydrogen: carbon monoxide ratio to be made. The estimated valve was approx. 2:1. The reactant concentrations are shown in Table 3A and the results obtained are shown in Table 3B.

EXAMPLE 7

The procedure described in Example 3 was followed except that the triphenylstibine was replaced by triphenylarsine. The reactant concentrations are shown in Table 3A and the results obtained are shown in Table 3B.

The results in Table 1 demonstrate that the addition of an inert liquid (chlorobenzene) to the cobalt acetate tetrahydrate/iodine/triphenylarsine catalysed reaction increases both the yield and selectivity to acetaldehyde. When triphenylarsine is replaced by triphenylphosphine ethanol is the major product. The cobalt acetate/iodine/triphenylstibine catalysed reaction (Table 2) gives high yields of acetaldehyde in the pesence of inert liquid (chlorobenzene). Comparison of Example 2 with Example 3 shows that the yield and selectivity to acetaldehyde is temperature and residence time dependent.

The results of Table 3 demonstrate the improvement in % molar selectivity to realisable acetaldehyde achieved by the addition of a non-polar solvent (octane), an oxygen-containing organic solvent (acetone) and an inert liquid (chlorobenzene). Examples 7 (Table 3) and 3 (Table 2) show that similar results are obtained using either triphenylarsine or triphenylstibine. Example 4 (Table 2) demonstrates that the addition of an acid derivative (methyl acetate) improves the % molar selectivity to realisable acetaldehyde.

TABLE 1A

| | Reactor Feed | | | |
|---|---|---|---|---|
| Example (a) | MeOH (Moles) (b) | Additive (Moles) (c) | Catalyst Components (Moles × $10^{-3}$) (d) | |
| Comparison Test | 2.00 | (None) | $Co(OAc)_2 4H_2O$ $AsPh_3$ $I_2$ | (25.1) (43.8) (12.6) |
| 1 | 0.80 | (0) Chlorobenzene (0.633) | $Co(OAc)_2 4H_2O$ $I_2$ $AsPh_3$ | (10.0) (5.0) (17.5) |
| Comparison Test 2 | 0.80 | Chlorobenzene (0.633) | $Co(OAc)_2 4H_2O$ $I_2$ $PPh_3$ | (10.0) (5.0) (17.5) |

In Tables 1 and 2 $Co(OAc)_2 4H_2O$ represents cobalt acetate tetrahydrate
$As(Ph)_3$ represents triphenylarsine
$Sb(Ph)_3$ represents triphenylstibine

TABLE 2A

| (a) | (b) | (c) | (d) | |
|---|---|---|---|---|
| Comparison Test 3 | 1.78 | Chlorobenzene (0.071) | $Co(OAc)_2 4H_2O$ $I_2$ $PPh_3$ | (22.5) (11.3) (39.4) |
| 2 | 1.81 | Chlorobenzene (0.071) | $Co(OAc)_2 4H_2O$ $I_2$ $SbPh_3$ | (22.5) (11.3) (39.4) |
| Comparison Test 4 | 2.00 | None | $Co(OAc)_2 4H_2O$ $I_2$ $SbPh_3$ | (24.9) (12.5) (43.7) |
| 3 | 1.81 | Chlorobenzene (0.073) | $Co(OAc)_2 4H_2O$ $I_2$ $SbPh_3$ | (22.5) (11.3) (39.4) |
| 4 | 1.20 | Methylacetate (0.40) | $Co(OAc)_2 4H_2O$ $I_2$ $SbPh_3$ | (14.9) (7.5) (25.8) |

TABLE 3A

| (a) | (b) | (c) | (d) | |
|---|---|---|---|---|
| 5 | 0.82 | Octane 0.40 | $Co(OAc)_2 4H_2O$ $I_2$ $AsPh_3$ | (10.0) (5.0) (17.5) |
| 6 | 1.80 | Acetone 0.147 | $Co(OAc)_2 4H_2O$ $I_2$ $AsPh_3$ | (22.5) (11.3) (39.4) |
| 7 | 1.80 | Chlorobenzene (0.072) | $Co(OAc)_2 4H_2O$ $I_2$ $AsPh_3$ | (22.5) (11.3) (39.4) |

TABLE 1B

| Example (e) | Reaction Temperature (°C.) (f) | Reaction Time (Hours) (g) | Realisable $CH_3CHO$ (h) | Realisable $CH_3COOH$ (i) | Realisable $C_2H_5OH$ (j) | % Molar Yields on Methanol Fed to Realisable $CH_3CHO$ (k) | % Molar Selectivity % MeOH (l) |
|---|---|---|---|---|---|---|---|
| Comparison Test 1 | 205 | 2 | 9.1 | 12.9 | 4.1 | 15.7 | 57.9 |
| 1 | 205 | 2 | 18.3 | 4.5 | 1.8 | 33.3 | 55.0 |
| Comparison Test 2 | 205 | 2 | 3.8 | 5.7 | 28.2 | 6.6 | 57.3 |

TABLE 2B

| (e) | (f) | (g) | (h) | (i) | (j) | (k) | (l) |
|---|---|---|---|---|---|---|---|
| Comparison Test 3 | 205 | 2 | 1.5 | 9.2 | 26.4 | 3.0 | 50.5 |
| 2 | 205 | 2 | 8.7 | 3.5 | 2.5 | 15.0 | 57.9 |
| Comparison Test 4 | 185 | 1 | 20.0 | 11.1 | 4.2 | 37.8 | 52.9 |
| 3 | 185 | 1 | 25.7 | 7.7 | 2.1 | 56.0 | 45.9 |
| 4 | 185 | 1 | 17.8 | 4.9 | 3.0 | 49.2 | 36.2 |

TABLE 3B

| (e) | (f) | (g) | (h) | (i) | (j) | (k) | (l) |
|---|---|---|---|---|---|---|---|
| 5 | 185 | 1 | 15.7 | 5.8 | 2.1 | 48.6 | 32.3 |
| 6 | 185 | 1 | 15.3 | 4.1 | 2.7 | 41.8 | 36.6 |
| 7 | 185 | 1 | 24.3 | 8.6 | 2.4 | 51.1 | 47.6 |

I claim:

1. A process for the production of acetaldehyde which process comprises reacting at a temperature of from about 150° to 250° C. and a pressure of from about 80 to 300 bar, methanol with hydrogen and carbon monoxide in the presence of:
   (a) a catalyst comprising cobalt, an iodide or a bromide and a compound of the formula

wherein X is arsenic, antimony or bismuth and A, B and C are individually an hydrocarbyl radical of 1 to 20 carbon atoms or any two of A, B and C together form an organic divalent cyclic ring system bonded to the X atom, and
   (b) at least one additive selective from:
      (i) an inert liquid selected from the group consisting of phenyl halides, thiophenes, long chain acids, and silicone oils;
      (ii) acids and derivatives thereof having the formula

wherein the substituent R is a hydrocarbyl group or an oxygen-containing hydrocarbyl group and the substituent X is the group —OR' wherein R' is a hydrogen atom, a hydrocarbyl group or an oxygen-containing hydrocarbyl group or X is the group —O—CO—$R^2$ wherein $R^2$ is a hydrocarbyl group or an oxygen-containing hydrocarbyl group;
      (iii) oxygen-containing organic compounds selected from the group consisting of aliphatic, alicyclic or aromatic ethers, aliphatic alcohols, aliphatic ketones and aliphatic aldehydes; and
      (iv) non-polar solvents selected from the group consisting of alkanes, benzene or alkyl substituted benzenes.

2. A process according to claim 1 wherein said additive (b) is an inert liquid selected from the group consisting of chlorobenzene, decanoic acid, polydimethyl siloxane fluids, methyl phenyl silicone fluids and a thiophene.

3. A process according to claim 2 wherein said compound having the formula (IV) is selected from the group consisting of triphenylarsine, triphenylstibine and tri-n-butyl arsine.

4. A process according to claim 1 wherein said compound having the formula (III) is selected from the group consisting of triphenylarsine, triphenylstibine, triphenyl bismuth, tri-n-butylarsine and tri-n-butylstibine.

5. A process according to either one of claims 1 and 2 wherein said elevated temperature is in the range 150° to 250° C., said elevated pressure is greater than 80 bars, the residence time is up to 8 hours, the molar ratio of carbon monoxide to hydrogen is in the range 2:1 to 1:3, the molar ratio of methanol to synthesis gas fed is in the range of from 10:1 to 1:20, the molar ratio of cobalt to iodine or bromine in said catalyst is in the range from 1:3 to 10:1, the molar ratio of cobalt to said compound of formula (II) or (IV) in said catalyst is in the range from 2:1 to 1:20, the molar ratio of iodine or bromine to said compound of formula (II) or (IV) in said catalyst is in the range from 2:1 to 1:10 and the molar ratio of cobalt to methanol is in the range from 1:10 to 1:1000.

6. A process according to either one of claims 1 and 2 wherein said elevated temperature is in the range 165° to 210° C., said elevated pressure is in the range from 100 to 300 bar, the residence time is in the range from 10 to 180 minutes, the molar ratio of carbon monoxide to hydrogen is in the range 3:2 to 2:3, the molar ratio of methanol to synthesis gas fed is in the range from 2:1 to 1:5, the molar ratio of cobalt to iodine or bromine in said catalyst is in the range from 1:1 to 5:1, the molar ratio of cobalt to compound of formula (II) or (IV) in said catalyst is in the range from 1:1 to 1:10, the molar ratio of iodine or bromine to said compound of formula (II) or (IV) in said catalyst is in the range from 1:1 to 1:8 and the molar ratio of cobalt to methanol is in the range from 1:40 to 1:800.

7. A process according to either one of claims 1 and 2 wherein said inert liquid is selected from from the group consisting of chlorobenzene, decanoic acid, a polydimethylsiloxane fluid and a methyl phenyl silicone fluid and is added in an amount such that the molar ratio of methanol to inert liquid is in the range from 30:1 to 1:10.

8. A process according to claim 1 wherein said acid or acid derivative of formula (I) is selected from from the group consisting of acetic acid, acetic anhydride, propionic acid, decanoic acid, phenylacetic acid, benzoic acid, methyl acetate and butyl acetate and is added in such an amount that the molar ratio of acid or derivative thereof to free methanol is up to 1.5:1.

9. A process according to claim 1 wherein said oxygen-containing organic compound is selected from from the group consisting of aliphatic, alicyclic or aromatic ethers, aliphatic alcohols, aliphatic ketones and aliphatic aldehydes and is added in an amount such that the molar ratio of methanol to the oxygen-containing organic compound is in the range from 20:1 to 1:3.

10. A process according to claim 1 wherein said oxygen-containing organic compound is selected from from the group consisting of 1,4-dioxane, tetrahydrofuran, di-n-propylether, diphenylether, acetone, acetaldehyde, n-propanol and n-butanol and is added in an amount such that the molar ratio of methanol to the compound is in the range from 20:1 to 1:3.

11. A process according to claim 1 wherein said non-polar solvent is selected from from the group consisting of alkanes, benzene or alkyl-substituted benzenes and is added in an amount such that the molar ratio of methanol to non-polar solvent is in the range from 30:1 to 1:10.

12. A process according to either one of claims 1 and 2 when carried out in a continuous manner.

13. A process according to claim 1 wherein each of A, B and C is an unsubstituted saturated aliphatic group, an unsubstituted saturated cycloaliphatic group or an unsubstituted aromatic hydrocarbyl group.

14. A process according to claim 1 or 2 wherein said inert liquid is added in an amount such that the molar ratio of methanol to inert liquid is in the range from 30:1 to 1:10.

* * * * *

UNITED STATES PATENT AND TRADEMARK OFFICE
CERTIFICATE OF CORRECTION

PATENT NO. : 4,225,517

DATED : September 30, 1980

INVENTOR(S) : Brian R. Gane

It is certified that error appears in the above-identified patent and that said Letters Patent are hereby corrected as shown below:

Col. 11 and 12, Table 1B, above columns (h), (i) and (j) - delete "Reaction", and insert --% Molar Yields on Methanol Fed-- in lieu thereof.

Col. 11 and 12, Table 1B, above column (k) - after "% Molar" delete "% Molar Yields on Methanol Fed", and insert --Selectivity-- in lieu thereof.

Col. 11 and 12, Table 1B, above column (l) - above "% MeOH" delete "Selectivity"; below "% MeOH" insert --Conversion--.

Signed and Sealed this

Fourth Day of August 1981

[SEAL]

Attest:

GERALD J. MOSSINGHOFF

Attesting Officer     Commissioner of Patents and Trademarks